United States Patent [19]

Sakashita et al.

[11] Patent Number: 5,215,897
[45] Date of Patent: Jun. 1, 1993

[54] PROCESS FOR PRODUCING L-AMINO ACIDS

[75] Inventors: Keiichi Sakashita, Akishima; Tetsuji Nakamura, Yokohama; Ichiro Watanabe, Yokosuka, all of Japan

[73] Assignee: Nitto Chemical Industries Co., Ltd., Japan

[21] Appl. No.: 525,302

[22] Filed: May 17, 1990

Related U.S. Application Data

[63] Continuation of Ser. No. 903,477, Sep. 4, 1986, abandoned.

[30] Foreign Application Priority Data

Sep. 4, 1985 [JP] Japan .................. 1-193867

[51] Int. Cl.$^5$ ............ C12P 13/04; C12P 13/22; C12N 9/78
[52] U.S. Cl. .................. 435/106; 435/108; 435/113; 435/116; 435/227; 435/828; 435/874; 435/244
[58] Field of Search ........... 435/108, 106, 113, 116, 435/227, 828, 874, 244

[56] References Cited

U.S. PATENT DOCUMENTS

| | | | |
|---|---|---|---|
| 3,386,888 | 6/1968 | Chibata et al. | 435/108 |
| 4,080,259 | 3/1978 | Boesten et al. | 435/280 |
| 4,366,250 | 12/1982 | Jallageas et al. | 435/108 |
| 4,443,548 | 4/1984 | Oshima et al. | 435/108 |
| 4,481,362 | 11/1984 | Nakai et al. | 548/498 |
| 4,497,957 | 2/1985 | Nakai et al. | 435/108 |

FOREIGN PATENT DOCUMENTS 0043211 6/1982 European Pat. Off.
1577087 10/1980 United Kingdom.

OTHER PUBLICATIONS

S. Yamada, K. Nabe, N. Izuo, K. Nakamichi and I. Chibata, Applied And Environmental Microbiology, Nov. 1981, pp. 773–778, vol. 42.

Primary Examiner—Irene Marx
Attorney, Agent, or Firm—Cushman, Darby & Cushman

[57] ABSTRACT

A process for producing an L-amino acid from the corresponding DL- and/or L-amino acid amide represented by the general formula:

$$R-\underset{NH_2}{\underset{|}{CH}}-CONH_2$$

wherein R is a substituted or unsubstituted alkyl group having one to 4 carbon atoms, a substituted or unsubstituted phenyl group, or a substituted or unsubstituted aralkyl group, by action of an enzyme having hydrolytic activity to L-amino acid amides which is produced by *Enterobacter cloacae* or *Pseudomonas sp.*

10 Claims, No Drawings

PROCESS FOR PRODUCING L-AMINO ACIDS

This is a continuation of application Ser. No. 06/903,477, filed on Sep. 4, 1986 which was abandoned upon the filing hereof.

BACKGROUND OF THE INVENTION

1. Field of the Invention

This invention relates to a process for producing an L-amino acid. More particularly, it relates to a process for producing an L-amino acid from DL- and/or L-amino acid amide by action of an enzyme prepared by a specific microorganism.

L-amino acids are important compounds as food additives, feed additives, and intermediates of medicines and various industrial chemicals.

2. Description of the Prior Art

In general, L-amino acids are produced by formentation or by optical resolution of DL-amino acids prepared in an organic synthetic-chemical method. Recently, there have been proposed and made practicable a large number of so-called chemico-enzymatic processes which comprise converting precursors inexpensively obtainable by chemical synthesis into L-amino acids by using enzymes.

Typical examples of the chemico-enzymatic processes for producing L-amino acids include, for example, a process comprising acting acylase produced by a microorganism on an N-acyl derivative of DL-amino acid (Japanese Patent Publication No. 22380/66), a process comprising acting hydantoinase produced by a microorganism on a hydantoin-substituted DL-amino acid derivative (Japanese Patent Publication No. 2274/79), a process comprising acting aspartase produced by a microorganism on fumaric acid (Japanese Patent Publication No. 18867/82 and Japanese Patent Application Kokai (Laid-Open) No. 140890/84), and a process comprising acting phenylalanine ammonia lyase produced by a microorganism on cinnamic acid (Appl. Environ, Microbiol. 42, 773 (1981)).

However, these processes involves problems, for example, complicated reaction systems, severe reaction conditions and expensive starting materials, and can stand improvement as industrial production processes.

Recently, there have also been proposed processes comprising reactions for producing various L-amino acids from the corresponding DL- or L-amino acid amides by using enzymes produced by microorganisms, for example, a process using an enzyme L-amidase produced by microorganisms belonging to Bacillus, Bacteridium, Micrococcus and Brevibacterium (publicized in Japanese Official Patent Gazette No. 500319/81) and a process using L-amidase produced by various yeasts and bacteria (Japanese Patent Application Kokai (Laid-Open) Nos. 13000/82, 159789/84 and 36446/85).

However, all of these processes involve a problem of low L-amidase activity, and they are experiment examples in which production reactions of L-amino acid were carried out by using a large amount of cells, or nothing but a finding that well-known strains belonging to various genera hydrolyze various DL- or L-amino acid amides to give the corresponding L-amino acids. Because of use of these microorganisms, they cannot possibly become economically advantageous production processes from the viewpoint of industrial processes for producing L-amino acids from DL- or L-amino acid amides by action of enzymes produced by microorganisms.

SUMMARY OF THE INVENTION

Under these circumstances, in order to obtain a microorganism capable of producing an enzyme having high L-amidase activity which permits efficient production of L-amino acids particularly from the corresponding DL-amino acid amides which can be prepared by chemical synthesis easily and inexpensively, the present inventors have conducted screening of microorganisms from soils, sludges and the like in various places. Consequently, the present inventors have found that an enzyme produced by microorganisms, *Enterobacter cloacae* N-7901, Pseudomonas sp. N-7131 and Pseudomonas sp. N-2211 has a very high L-amidase activity and is very effective in achieving the object of this invention, whereby this invention has been accomplished.

That is to say, the gist of the invention is a process for producing an L-amino acid which comprises producing an L-amino acid from the corresponding DL- and/L-amino acid amide represented by the general formula:

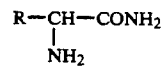

wherein R is a substituted or unsubstituted alkyl group having one to 4 carbon atoms, a substituted or unsubstituted phenyl group, or a substituted or unsubstituted aralkyl group, by action of an enzyme having hydrolytic activity to L-amino acid amides which is produced by a microorganism, *Enterobacter cloacae* N-7901 (FERM BP No. 873), Pseudomonas sp. N-7131 (FERM BP No. 874) or Pseudomonas sp. N-2211 (FERM BP No. 875).

DETAILED DESCRIPTION OF THE INVENTION

The microorganisms used in this invention are those newly isolated and named by the present inventors as described above and were deposited in Fermentation Research Institute, Agency of Industrial Science and Technology (Bikoken), Ministry of International Trade and Industry as FERM BP No. 873 (*Enterobacter cloacae* N-7901), FERM BP No. 874 (*Pseudomonas* sp. N-7131) and FERM BP No. 875 (*Pseudomonas sp. N-2211*) according to Budapest Treaty, respectively.

Micological properties of these microorganisms are as follows:

| N-7901 strain | |
|---|---|
| (1) Morphological properties | |
| Bacillus | 0.8~1.2 × 1.0~1.5 μm |
| Flagellum | mono or multitrichous |
| Motility | + |
| Gram staining | negative |
| (2) Physiological properties | |
| Reduction of nitrate | + |
| Denitrification | − |
| MR test | − |
| VP test | + |
| Production of indole | − |
| Production of hydrogen sulfide | − |
| Utilization of citrate | + |
| Production of pigment | − |
| Urease | − |
| Oxidase | − |
| Catalase | + |

| Ranges for growth | |  |
| --- | --- | --- |
| PH | 4-10 | |
| Optimum temperature | 35-37° C. | |
| Behavior toward oxygen | facultatively | |
| anaerabic | | |
| O-F test | F | |

| Production of acid and gas from sugars | Production of acid | Production of gas |
| --- | --- | --- |
| Adonitol | − | − |
| Arabinose | + | + |
| Xylose | + | + |
| Glucose | + | + |
| Mannose | + | + |
| Fructose | + | + |
| Galactose | ± | + |
| Maltose | + | + |
| Sucrose | ± | ± |
| Lactose | + | + |
| Raffinose | + | |
| Rhamnose | + | |
| Glycerol | + | + |
| Sorbitol | + | + |
| Mannitol | + | + |
| Inositol | − | − |
| Dulcitol | − | − |

(3) Other properties

| | |
| --- | --- |
| Decomposition of starch | − |
| Decomposition of gelatin | − |
| Decomposition of urea | slight |
| Utilization of malonate | + |
| Decarboxylation of lysine | − |
| Decarboxylation of ornithine | + |
| Deamination of phenylalanine | − |
| Arginine dihydrolase | + |
| βGalactosidase | + |
| Resistance to potassium cyanide | + |

N-7131 strain (1) Morphological properties

| | |
| --- | --- |
| Bacillus | |
| Flagellum | polar mono- or multitrichous |
| Motility | + |
| Endospore | None |
| Gram staining | negative |

(2) Physiological properties

| | |
| --- | --- |
| Denitrification | + |
| Production of indole | − |
| Production of hydrogen sulfide | − |
| Utilization of citrate | + |

Production of pigment

| | |
| --- | --- |
| water-soluble pigment | − |
| fluorescent pigment | − |
| Urease | + |
| Oxidase | + |
| Catalase | + |
| Growth at 40° C. | − |
| O-F test | O |

| Production of acid and and gas from sugars | Production of acid | Production of gas |
| --- | --- | --- |
| Xylose | + | |
| Glucose | + | − |
| Mannose | + | |
| Galactose | + | |
| Lactose | − | |
| Mannitol | + | |

Utilization

| | |
| --- | --- |
| Glucose | + |
| Fructose | + |
| L-Arabinose | + |
| Sucrose | − |
| Malonate | − |
| Ethanol | − |
| Trehalose | − |
| meso-Inositol | + |
| β-Alanine | + |
| DL-Arginine | + |

(3) Other properties

| | |
| --- | --- |
| Decomposition of starch | − |
| Decomposition of gelatin | − |
| Decomposition of urea | − |
| Accumulation of poly-β-hydroxybutyrate | + |
| Arginine dihydrolase | − |
| Aminopeptidase | + |
| Growth in the presence of 6.5% NaCl | − |

N-2211 strain (1) Morphological properties

| | |
| --- | --- |
| Bacillus | |
| Flagellum | polar monotrichous |
| Motility | + |
| Endospore | None |
| Gram staining | negative |

(2) Physiological properties

| | |
| --- | --- |
| Denitrification | slight |
| Production of indole | − |
| Production of hydrogen sulfide | − |
| Utilization of citrate | + |

Production of pigment

| | |
| --- | --- |
| water-soluble pigment | slight |
| fluorescent pigment | − |
| Urease | + |
| Oxidase | + |
| Catalase | + |
| Growth at 40° C. | − |
| O-F test | O |

| Production of acid and gas from sugars | Production of acid | Production of gas |
| --- | --- | --- |
| Xylose | + | |
| Glucose | + | − |
| Mannose | + | |
| Galactose | + | |
| Lactose | − | |
| Mannitol | slight | |

Utilization

| | |
| --- | --- |
| Glucose | + |
| Fructose | + |
| L-Arabinose | + |
| Sucrose | − |
| Malonate | − |
| Ethanol | − |
| Trehalose | − |
| meso-Inositol | slight |
| β-Alanine | slight |
| DL-Arginine | − |

(3) Other properties

| | |
| --- | --- |
| Decomposition of starch | − |
| Decomposition of gelatin | − |
| Decomposition of urea | + |
| Accumulation of poly-β-hydroxybutyrate | slight |
| Arginine dihydrolase | −. |
| Aminopeptidase | + |
| Growth in the presence of 6.5% NaCl | − |

By reference to Bergy's Manual of Determinative Bacteriology, 8th ed. for the mycological properties described above, N-7901 strain was identified as *Enterobacter cloacae* and N-7131 and N-2211 strains as bacterium belonging to Pseudomonas. N-7131 strain accumulated poly-β-hydroxybutyrate in the cells, was negative in both growth at 40° C. and arginine dihydrolase, and was positive in denitrification. Although this strain had untypical properties with respect to utilization of sugars and the like, it seems to be *Pseudomonas solanacearum* or a strain nearly related thereto.

As is obvious to the artisan in the art, mutants of the above-mentioned strains can also be used. These mutants can easily be obtained by treatment with a mutagent such as nitrogen mustard and the like.

For culturing the above-mentioned microorganism to allow the same to produce the enzyme of this invention, it is sufficient that said microorganism is aerobically cultured by using a conventional medium containing a carbon source, a nitrogen source, inorganic salts and an organic nutrient.

As the carbon sources, there can be properly used sugars such as glucose, fructose, sucrose, maltose and the like, organic acids such as acetic acid, citric acid and the like, etc. The using amount thereof is usually 0.1 to 10% (by weight, hereinafter the same applied) based on the weight of the medium. As the nitrogen sources, there can be used ordinary natural nitrogen sources such as peptone, meat extract, yeast extract, corn steep liquor, protein hydrolyzates, amino acids and the like, and ammonium salts of various organic or inorganic acids, etc. As the inorganic salts, there are, if necessary, used properly $KH_2PO_4$, $K_2HPO_4$, $Na_2HPO_4$, NaCl, $CaCl_2$, $MgSO_4.7H_2O$ and ions of heavy metals such as Fe, Mn, Zn, Co and the like. In this case, addition of a small amount of an aliphatic amide having 2 to 5 carbon atoms (e.g., acetamide, propionamide, butylamide, or succino-amide) is effective in inducing high enzymatic activity, and the adding amount thereof is usually preferably 0.01% or more, particularly preferably about 0.1 to about 0.5% based on the weight of the medium.

The culture is aerobically carried out at pH 5 to 10 at a temperature of 20° to 40° C. for one to 5 days.

This invention utilizes the action of an enzyme produced by a microorganism and the enzymic action can be attained by incubating a mixture of DL and/or L-amino acid amide and any of culture broth of a microorganism obtained by the culture carried out in the manner described above, separated viable cells, microorganism-derived fractions (e.g., sonificated cells and cell extract), and immobilized cells or extracts thereof obtained by immobilizing cells or microorganism-derived fraction on polyacrylamide, carageenan or the like by a conventional method. All of these forms for use can be applied to this invention.

The hydrolysis (the incubation with said amide) is usually carried out under the following conditions: the concentration of DL- and/or L-amino acid amide of the above general formula, 0.5 to 50% (the substrate solution for reaction may be slurry); the amount of the microorganism or the like, 0.01 to 10% (in terms of dried cells) based on the weight of the reaction solution; the reaction temperature, 20° to 60° C.; pH, 6 to 11; the reaction time, 5 min. to 100 hours.

The L-amino acid thus produced and accumulated in the reaction solution can be separated and purified by a combination of well-known methods such as ion exchange method and the like.

The DL- and/or L-amino acid amide used in this invention is a compound represented by the above general formula in which R is a substituted or unsubstituted alkyl group having one to 4 carbon atoms, a substituted or unsubstituted phenyl group, or a substituted or unsubstituted aralkyl group. The substituents include mercapto group, hydroxyl group, amino group, carboxyl group, phenyl group, indolyl group, pyridyl group, imidazolyl group, etc.

The L-amino acid produced according to this invention include, for example, L-phenylalanine, L-tryptophan, L-leucine, L-methionine, L-serine, etc.

This invention is concretely explained below referring to Examples, which are not by way of limitation but by way of illustration. In each Example, the identification and quantitation of L-amino acid were conducted by thin-layer chromatography followed by examination of positions of ninhydrin coloration, and high performance liquid chromatography.

EXAMPLE 1

Shake culture of N-7901 strain was carried out at 30° C. for 48 hours by using a medium having the following composition:

| Sucrose | 1% |
|---|---|
| Meat extract | 0.5% |
| | $MgSO_4.7H_2O$ 0.01% |
| | $FeSO_4.7H_2O$ 0.001% |
| Inorganic salts | $MnSO_4.4H_2O$ 0.001% |
| | $CaCl_2.2H_2O$ 0.001% |
| | $ZnSO_4.7H_2O$ 0.0001% |
| Propionamide | 0.5% |
| pH 5 | |

One hundred milliliters of the culture broth was centrifuged and the viable cells thus obtained were suspended in 50 ml of Tris-HCl buffer (pH9). Subsequently, 1 ml each of the resulting suspensions was added to 4 ml of a 0.5% aqueous solution (prepared by using Tris-HCL buffer (ph9)) of each of the various amides shown in Table 1 and the resulting mixture solutions were incubated, respectively at 30° C. for 10–15 minutes. After the removal of bacterial cells, the amounts of L-amino acid produced and the whole amino acid produced were measured to obtain the results shown in Table 1.

TABLE 1

| Starting amino acid amide | Amino acid produced | Reaction time (min) | Yield (based on DL-form charged (%)) | L-amino acid/amino acid produced (%) |
|---|---|---|---|---|
| DL-Leucine amide | L-Leucine | 10 | 50 | 100 |
| DL-Methionine amide | L-Methionine | 15 | 13 | 100 |
| DL-Serine amide | L-serine | 15 | 3 | 100 |
| DL-Phynyl-alanine amide | L-Phynyl-alanine | 15 | 50 | 100 |
| DL-Tryptophan amide | L-Tryptophan | 15 | 34 | 100 |
| DL-Phenyl-glycine amide | L-Phenyl-glycine | 15 | 48 | 100 |

EXAMPLE 2

Shake culture of N-2211 strain was carried out at 30° C. for 48 hours by using a medium having the following composition:

| Glycerol | 1% |
|---|---|
| Yeast extract | 0.05% |
| | $MgSO_4.7H_2O$ 0.01% |
| | $FeSO_4.7H_2O$ 0.001% |
| Inorganic salts | $MnSO_4.4H_2O$ 0.001% |
| | $CaCl_2.2H_2O$ 0.001% |
| | $ZnSO_4.7H_2O$ 0.0001% |
| Isobutylamide | 0.5% |
| pH 7 | |

Thereafter, the procedure in Example 1 was repeated, except that the reaction time was changed to 1 to 3 hours, to obtain the results shown in Table 2.

TABLE 2

| Starting amino acid amide | Amino acid produced | Reaction time (min) | Yield (based on DL-form charged) (%) | L-amino acid/amino acid produced (%) |
|---|---|---|---|---|
| DL-Leucine amide | L-Leucine | 1 | 50 | 100 |
| DL-Methionine amide | L-Methionine | 3 | 19 | 100 |
| DL-Serine amide | L-Serine | 3 | 6 | 100 |
| DL-Phenylalanine amide | L-Phenylalanine | 3 | 24 | 100 |
| DL-Tryptophan amide | L-Tryptophan | 3 | 50 | 100 |
| DL-Phenylglycine amide | L-Phenylglycine | 3 | 20 | 100 |

EXAMPLE 3

Shake culture of N-7131 strain was carried out at 30° C. for 48 hours by using a medium having the following composition:

| Glycerol | 1% |
|---|---|
| Meat extract | 0.5% |
| Inorganic salts | $MgSO_4 \cdot 7H_2O$ 0.01% |
| | $FeSO_4 \cdot 7H_2O$ 0.001% |
| | $MnSO_4 \cdot 4H_2O$ 0.001% |
| | $CaCl_2 \cdot 2H_2O$ 0.001% |
| | $ZnSO_4 \cdot 7H_2O$ 0.0001% |
| Isobutylamide | 0.5% |
| pH 7 | |

Thereafter, the procedure in Example 2 was repeated to obtained the results shown in Table 3.

TABLE 3

| Starting amino acid amide | Amino acid produced | Reaction time (min) | Yield (based on DL-form charged) (%) | L-amino acid/amino acid produced (%) |
|---|---|---|---|---|
| DL-Leucine amide | L-Leucine | 1 | 50 | 100 |
| DL-Methionine amide | L-Methionine | 3 | 31 | 100 |
| DL-Serine amide | L-Serine | 3 | 0.3 | 100 |
| DL-Phenylalanine amide | L-Phenylalanine | 3 | 50 | 100 |
| DL-Tryptophan amide | L-Tryptophan | 3 | 48 | 100 |
| DL-Phenylglycine amide | L-Phenylglycine | 3 | 48 | 100 |

EXAMPLE 4

When 1 ml of a suspension of N-7901 strain obtained in the same manner as in Example 1 was added to 4 ml of a 1.25% L-phenylalanine amide solution and the resulting mixture was subjected to reaction at 40° C. for 15 minutes, the yield of phenylalanine was 75% and the L-phenylalanine produced is the L-form alone.

What is claimed is:

1. A process for producing an L-amino acid comprising:
   (a) contacting a DL- or L-amino acid amide selected from the group consisting of leucine amide, methionine amide, serine amide, phenylalanine amide, tryptophan amide, phenylglycine amide and valine amide, with a culture of microorganisms selected from the group consisting of Enterobacter cloacae N-7901 (FERM BP No. 873), Pseudomonas sp. N-7131 (FERM BP No. 874), Pseudomonas sp. N-2211 (FERM BP No. 875), and mutant strains thereof that produce L-amidase activity, wherein said culture of microorganisms is cultured with 0.1% to 0.5% by weight of an aliphatic amide having 2 to 5 carbon atoms and wherein said contacting is effected at a pH in the range of from 6 to 11, at a reaction temperature in the range of from 20° C. to 60° C., and with a reaction time in the range of from 5 minutes to 100 hours, and
   (b) recovering said L-amino acid.

2. The process according to claim 1, wherein said L-amino acid is L-leucine and said DL- or L-amino acid amide is DL- or L-leucine amide.

3. The process according to claim 1 wherein said L-amino acid is L-methionine and said DL- or L amino acid amide is DL- or L-methionine amide.

4. The process according to claim 1 wherein said L-amino acid is L-serine and said DL- or L-amino acid amide is DL- or L-serine amide.

5. The process according to claim 1 wherein said L-amino acid is L-phenylalanine and said DL- or L-amino acid amide is DL- or L-phenylalanine amide.

6. The process according to claim 1 wherein said L-amino acid is L-tryptophan and said L- or DL-amino acid amide is DL- or L-tryptophan amide.

7. The process according to claim 1 wherein said L-amino acid is L-phenylglycine and said L- or DL-amino acid amide is DL- or L-phenylglycine amide.

8. The process according to claim 1 wherein said L-amino acid is L-valine and said L- or DL-amino acid amide is DL- or L-valine amide.

9. The process for producing an L-amino acid according to claim 1 wherein said culture of microorganisms is a culture of Enterobacter cloacae N-7901 (FERM BP No. 873).

10. A process for producing an L-amino acid comprising:
   (a) contacting a DL- or L-amino acid amide selected from the group consisting of leucine amide, methionine amide, serine amide, phenylalanine amide, tryptophan amide, phenylglycine amide and valine amide, with a culture of microorganisms selected from the group consisting of Pseudomonas sp. N-7131 FERM BP No. 874), Pseudomonas sp N-2211 FERM BP No. 875), and mutant strains thereof that produce L-amidase activity, wherein said culture of microorganisms is cultured with 0.1% to 0.5% by weight of an aliphatic amide having 2 to 5 carbon atoms, wherein said contacting is effected at a pH in the range of from 6 to 11, at a reaction temperature in the range of from 20° C. to 60° C., and with a reaction time in the range of from 5 minutes to 100 hours, and
   (b) recovering said L-amino acid.

* * * * *

UNITED STATES PATENT AND TRADEMARK OFFICE
CERTIFICATE OF CORRECTION

PATENT NO. : 5,215,897
DATED : June 1, 1993
INVENTOR(S) : SAKASHITA et al.

It is certified that error appears in the above-indentified patent and that said Letters Patent is hereby corrected as shown below:

On the title page, change "[73] Assignee: Nitto Chemical Industries Co., Ltd., Japan" to --Nitto Chemical Industries Co., Ltd., and Mitsubushi Rayon Co., Ltd., both of Tokyo, Japan--.

Signed and Sealed this

Second Day of August, 1994

Attest:

BRUCE LEHMAN

Attesting Officer     Commissioner of Patents and Trademarks